United States Patent [19]

Roizenblatt

[11] Patent Number: 4,650,460

[45] Date of Patent: Mar. 17, 1987

[54] PNEUMATIC MODULE FOR INTRAOCULAR MICROSURGERY

[76] Inventor: Jaime Roizenblatt, Rua Baronesa de Itu, 363, 01231 - Sao Paulo, SP, Brazil

[21] Appl. No.: 746,361

[22] Filed: Jun. 19, 1985

[30] Foreign Application Priority Data

Jun. 28, 1984 [BR] Brazil .................................. 8403165

[51] Int. Cl.$^4$ .............................................. A61B 17/32
[52] U.S. Cl. ....................................... 604/22; 128/305
[58] Field of Search .................... 128/305; 604/22, 27, 604/35

[56] References Cited

U.S. PATENT DOCUMENTS

| | | | |
|---|---|---|---|
| 2,710,005 | 6/1955 | McConnell | 604/35 |
| 3,776,238 | 12/1985 | Peyman | 128/305 |
| 3,815,604 | 6/1974 | O'Malley et al. | 128/305 |
| 3,884,238 | 5/1975 | O'Malley et al. | 128/305 |
| 4,041,947 | 8/1977 | Weiss et al. | 604/22 |
| 4,099,529 | 7/1978 | Peyman | 128/305 |
| 4,314,560 | 2/1981 | Helfgott et al. | 128/305 |

OTHER PUBLICATIONS

Michaelson Transcleral Div. of Mid-Vitreous Membrane Under Visual Control, 44 Brit. J. Opth. 634 (1960).
Tolentino et al, Vitreous Surgery—XII New Instrumentation for Vitrectomy, 93 Arch. Opth. 667 (1975).
Freeman et al, Vitreous Surgery-II Instrumentation and Technique, 77 Arch. Opth. 681 (1967).
Cibis, Vitreous Transfer and Silicone Injection, 68 Trans. Amer. Acad. Opth. & O. 983 (1964).
Peyman et al, Experimental Vitrectomy—Instrumentation and Surgical Technique, 86 Arch. Opth. 548 (1971).
Wang, Microsurgical Instrumentation for Vitrectomy: Parts I and II, 8 Jour. Clin. Engin. 321 (1983); 9 Id. at 63 (1984).

Primary Examiner—Carlton R. Croyle
Assistant Examiner—Theodore Olds
Attorney, Agent, or Firm—Koppel & Harris

[57] ABSTRACT

An electro-pneumatic module is provided that permits the gradual control of the level of air pressure pulses injected into pneumatic vitrectomy probes used in intraocular microsurgical procedures. This invention permits the interchangeable use of the different pneumatic probe models according to their working pressure. The module generates in an alternating mode a flow of air pressure that can be varied from 0 to 30 p.s.i. or more, intercalated with a vacuum flow. This alternate air pulse is blown in a variable frequency of 0 to 800 times per minute into the piston of vitrectomy probes, moving in this way the internal cutting needle back and forth. The module contains also an gradually adjustable aspirating system responsible for sucking out the material sectioned by the chopping action of the internal needle.

1 Claim, 1 Drawing Figure

PNEUMATIC MODULE FOR INTRAOCULAR MICROSURGERY

BACKGROUND OF THE INVENTION

1. Field of the Invention:

This invention relates to a pneumatic module that allows a gradual adjustment of the level of air pressure pulses injected into the piston of any of the regular pneumatic vitrectomy probes available for intraocular microsurgical procedures.

2. Prior Art:

Until 1958 very few opthalmologists would risk surfically manipulating the vitreous gel. Although the vitreous gel comprises 70% of the eye weight and volume, it was considered a "prohibited area" for the great majority of eye surgeons because most interventions in which vitreous loss occurred were followed by complications such as corneal edema, glaucoma, retinal detachment, intraocular hemorrhage and even atrophy of the ocular globe.

The vitreous gel is composed of 99% water, and the remaining 1% includes two main components: collagen fibers and hyaluronic acid. The vitreous owes its characteristic consistency to its sincicial structure in which long collagen chains form the frame for dispersion of hyaluronic acid molecules. The last two components, collagen and hyaluronic acid, are bound in the vitreous gel to large amounts of water. This fact and the absence of vessels in the vitreous space guarantees the excellent light transmission properties and the inelasticity of the gel. The external surface of the vitreous is called the hyaloid membrane, a form of densified vitreous gel, which is in contact with the following eye structures: the posterior capsule of the crystalline, the pars plana epithelium, the retina and the optic nerve.

The many instances of light being prevented from normal focusing on the retina due to vitreous alterations have long stimulated the imagination of eye doctors on how to intervene upon these altered states. Examples of vitreous alteration are vitreous bands causing traction and detachment of the retina, vitreous opacification due to the inflammatory or infectious processes, presence of foreign bodies in the vitreous space, eye perforations causing vitreous loss, vitreous band formations and many other circumstances.

In 1958 Shafer tried to substitute diseased vitreous (D.M. Shafer, "The Treatment of Retinal Detachment by Vitreous Implant," 61 Transactions American Academy Ophthalmology Otolaryngol. pp. 194–200 (1958). An instrument for cutting vitreous bands was devised by Michaelson in 1960 (Michaelson, "Transcleral Division of Mid-Vitreous Membrane Under Visual Control," 44 British Journal of Ophthalmology pp. 634–635 (1960). The replacement of vitreous by silicon oil was performed in 1964 by Cibis, (P. A. Cibis, "Vitreous Transfer and Silicon Injection," 68 Transaction American Academy Ophthalmology Otolaryng., pp. 983–997 (1964). Freeman, Schepens and Anastopoulus started with their vitreous scissors in 1967 ("Vitreous Surgery—II., Instrumentation and Technique." 77 Arch. Ophthalmol. pp. 681–682 (1967).

The first successful and efficient mechanism for closed intraocular microsurgical procedures and vitreous cutting and removing was developed by Machemer, Buettner and Norton in 1970, with the vitreous cutter-sucker infusion instrument (Vitrectomy—American Academy of Ophthalmology and Otolaryng—Las Vegas 1970). Machemer was the first to conceive the idea of producing small pars plana incisions in order to introduce his probe for vitreous surgery. After the work of Machemer, other models were created, but basically all these probes together with their activating units and accessories are basically intended for cutting and removing abnormal vitreous or other unwanted tissue or substance (e.g. blood, fibrous tissue) from the vitreous cavity while keeping the intraocular pressure carefully controlled to minimize possible trauma for the globe. When the surgeon finds it necessary to remove the diseased vitreous or other extraneous matter from within the eye, this removal must be accomplished without damage to the retina, to the optic nerve or to their associated blood vessels. This is no easy task as the vitreous cannot be cut by a scalpel or other similar instrument because it is relatively tough and simply folds over the edge of the knife and refuses to be severed.

One can cut the vitreous gel in several ways:

(a) Mechanically, in which the apposition of two concentric needles, the inner one having a chopping, rotating or oscillating action against the outer tube cuts the vitreous gel and strands. After being cut the vitreous to be removed is drawn inside the inner tube by way of suction and in this way eliminated from the eye.

(b) Ultrasonically using phacoemulsification units, which emulsify and than aspirate the diseased vitreous (L. J. Girard, "Ultrasonic Fragmentation for Vitrectomy and Associated Surgical Procedures," 81 Trans. Am. Acad. Ophthalmol. Otol. p. 432 (1976).

(c) With laser energy (for example, cutting vitreous strands with the YAG neodymium laser).

In the previously mentioned Machemer instrument, the two tubes are mounted concentrically, both having a hole close to the end. The inner tube of the Machemer instrument rotates against the inner surface of the outer, stationary tube. At the moment the two holes appose one another, vitreous is sucked inside the internal needle. In this model the rotating or oscillating movement of the internal needle might cause problems due to a possible traction it can produce upon the collagen fibers, which can result in a pulling effect and injury to the retina. In the Machemer model a small electric motor at the rear end of the probe creates the rotating movement. In the vitrectomy probe described by Peyman ("Experimental Vitrectomy," 86 Arch Ophthal. p. 548 (Nov. 1971)), the inner tube oscillates and chops vitreous. A small, electric solenoid oscillates the inner tube. A few modifications and improvements in the probe models have been introduced with the passage of time, resulting in the appearance of new models:

(a) Chrome-plated internal needle, with a very fine tip finishing (the S.I.T.E. model, J. Federman, 7 Ophthalmic Surgery p. 82 (1976).

(b) Internal needle that has a precision fit as in the Grieshaber model, instead of being spring loaded as in the Machemer model, (Grieshaber-Schepens vitrectomy unit)

(c) Use of a rotating helical trunco-conical shaped internal needle precision fitted to the external needle, so that both tubes have a cutting blade surface, promoting a self-sharpening action and therefore reducing the wear of the cutting surface of the internal needle-Vitreous Nibbler (F. I. Tolentino, et al., "Vitreous Surgery—XII New Instrumentation for Vitrectomy," 93 Arch. Ophthalmol., p. 667 (1975).

A rotary cutting element is present in most of the previous vetrectomy instruments described. Rotary instruments, however, tended to have undesirable pulling or shearing effects on the tissue being severed. Efforts to avoid these effects led to the development of linearly reciprocating cutting instruments, an early sample of which is the initial model described by Peyman at al. 86 Arch. Ophthal. p. 548 (1971), in which cutting is performed by the chopping action of the sharpened end of the inner tube against the plane interior end of the outer tube. Suction applied to the inner tube causes the severed tissue to enter the hole in the outer tube, thus removing the severed bits of tissue from the eye. The necessary powered reciprocation of the inner tube relative to the fixed outer tube is provided by a small electrical solenoid, the oscillation rate of which can be varied. A description of this handpiece can also be found in Peyman, U.S. Pat. No. 3,776,238.

Although electrical solenoid devices provide a readily adjustable source of linear reciprocating motion, they also possess numerous drawbacks that limit their utility in a surgical environment. They tend to be relatively heavy, for example, which renders the handpiece somewhat incovenient to manipulate. During sustained operations, solenoid devices also tend to generate significant amounts of heat, which can damage delicate tissues. Moreover, since the solenoid is an integral part of the handpiece and must be supplied with an electrical current, an additional hazard is present.

Pneumatic power sources possess none of the foregoing disadvantages. Pneumatic devices are readily adaptable to linear reciprocating operations, do not inherently generate heat, and can be constructed from light weight materials. To the extent that electrical controls are necessary, they can be confined to a pneumatic power unit that is connected to the handpiece by an insulating pneumatic supply line and are well isolated from the surgical field. Pneumatic devices also tend to produce more evenly modulated power pulses than electrical solenoid devices. These factors make pneumatic devices ideal as power sources for powered vitrectomy instruments, and a number of pneumatically operated handpieces have been developed for ophthalmic use. With the continual refinement of endophthalmic surgical techniques and the proliferation of specialized reciprocating instruments based on the previously described prototype of Peyman, there has arisen a need for a pneumatic handpiece which is compact for convenient manipulation during delicate surgical procedures, simple in construction, safe to operate in a surgical environment, versatile in the sense of accommodating a number of different endophthalmic instruments in an interchangeable manner an reasonably priced.

One known type of pneumatic handpiece is described in O'Malley U.S. Pat. Nos. 3,815,604, 3,884,237 and 3,884,238. The disclosed handpiece consists generally of a cylindrical housing, an end cap for receiving one end of a projecting sharp-edged stainless steel tube, and a piston within the housing for providing reciprocating motion to a second stainless steel tube coaxially arranged within the first tube. The inner tube is sharpened at its distal end and the outer tube is provided with a lateral sharpened distal opening to form a push-type cutter. The inner tube is attached directly to the piston and extends axially through to the opposite side thereof for connection to a flexible evacuation line which passes out the back of the handpiece. The alternate air and suction pulses required for reciprocating the piston are supplied through a large-diameter tube also connect to the back of the handpiece.

O'Malley also introduced the idea of creating separate entrances for the infusion and illumination devices and for the cutting probe. In this way the bi-manual techniques for endophthalmic surgery were started and were promptly accepted because they made possible a better control of the eye position in surgical procedures. The other advantage was the less deleterious effect it had upon the eye creating three small 1 mm incisions in the pars plana instead of large 4-5 mm holes for entrance of large probes concentrically mounted, containing in one block the irrigation, illuminating and cutting aspects. The capability of moving the cutting needle by pneumatic means proved to be superior because of its dependability and simplicity. As a result, pneumatic systems have replaced solenoid systems to move the cutting needle.

At least three of the major handpieces available in the market are propelled by pneumatic means: the Ocutome probe of O'Malley, the "Vitrophage" probe of Peyman and the "Microvit" probe of the Storz Company (Wang, "Microsurgical Instrumentation for Vitrectomy: Part II," 9 (1) Journ. Clinical Engin. pp. 63-71 (1984)). The main difference in the propelling aspect of those probes is the level of air pressure necessary to move their internal needles, and the mechanism of bringing the cutting needle back to the rest position after being moved forward. In the Ocutome probe, a dual spring and suction mechanism returns the internal needle to the rest position. The return in the Vitrophage probe depends entirely on a spring action.

SUMMARY OF THE INVENTION

It is the object of the present invention to provide an improved pneumatic module for intraocular microsurgery that can interchangeably drive any of the different pneumatic intraocular microsurgical probes already developed, by providing them with different levels of pressure, necessary to move their inner needles forward, according to their pressure specifications and by providing them with a mechanism by which the cutting needle is returned to the rest position.

The pneumatic module was designed to provide variable suction, which is controlled by one foot pedal. A second pedal starts and stops the cutting device, which cuts at a variable cutting speed between 0 and 800 cycles per minute. The speed is controlled at the console. A third pedal is used when cutting and suction are needed together. Maximum suction for aspirating severed material is preset on the console.

The scope of developing the present pneumatic module was to have a unit that could accept any of the different pneumatic handprobes already developed and others that will probably be developed in the future. For this unit to operate the different pneumatic probes it is only necessary to adjust a knob in the console, thus controlling the level of air pressure that is admitted into the piston of the different probes. The return of the internal needle of the probe to the rest position in each back-and-forth cycle can be controlled in this new module in either way: by a spring action only or by a dual spring and suction mechanism. Another feature of the present invention is its portability, being easily carried with one hand, and its small size and weight. This module normally operates with the air pressure and vacuum sources regularly available in operating rooms, although it can also be attached to a pressure and a vacuum pump. This module permits gradual control of suction of the severed material, and this control is obtained through a foot pedal. In the front panel of the unit there is also a knob that pre-sets the maximum aspiration level that will be obtained after total depression of the suction pedal, thus adding a safety mechanism by preventing excessive aspiration in very delicate cases, such as when the surgeon is working too close to the retina.

Very high levels of aspiration are occasionally needed during intraocular surgery, and the present apparatus has also the capability of supplying the probe with such high levels of suction (300 mm Hg or more). Due to the disposition of the components of the present invention, there is no residual suction at the tip of the handprobe in the precise moment in which depression of the suction pedal is relieved. This eliminates complicated mechanisms existent in other pneumatic consoles for venting residual suction on the tip of the probe, during intraocular surgery. Residual suction at the probe could have catastrophic results such as aspiration of normal tissue like retina if not controlled during intraocular surgery.

Another feature of the present invention is the possibility of controlling the internal needle within a variable frequency from 0 to 800 cuts per minute. The cutting speed can also be increased above 800 times per minute with a slight modification in the module.

This module activates different pneumatic vitrectomy probe models used in intraocular microsurgical procedures. This equipment is used in the treatment of vitreous hemorrhages of any origin, perforating wounds of the ocular globe, vitreous biopsy, congenital and complicated cataracts, retinal detachments with an important vitreous traction component, retrolental fibroplasia, intraocular foreign bodies and many other illnesses.

Figure 1:
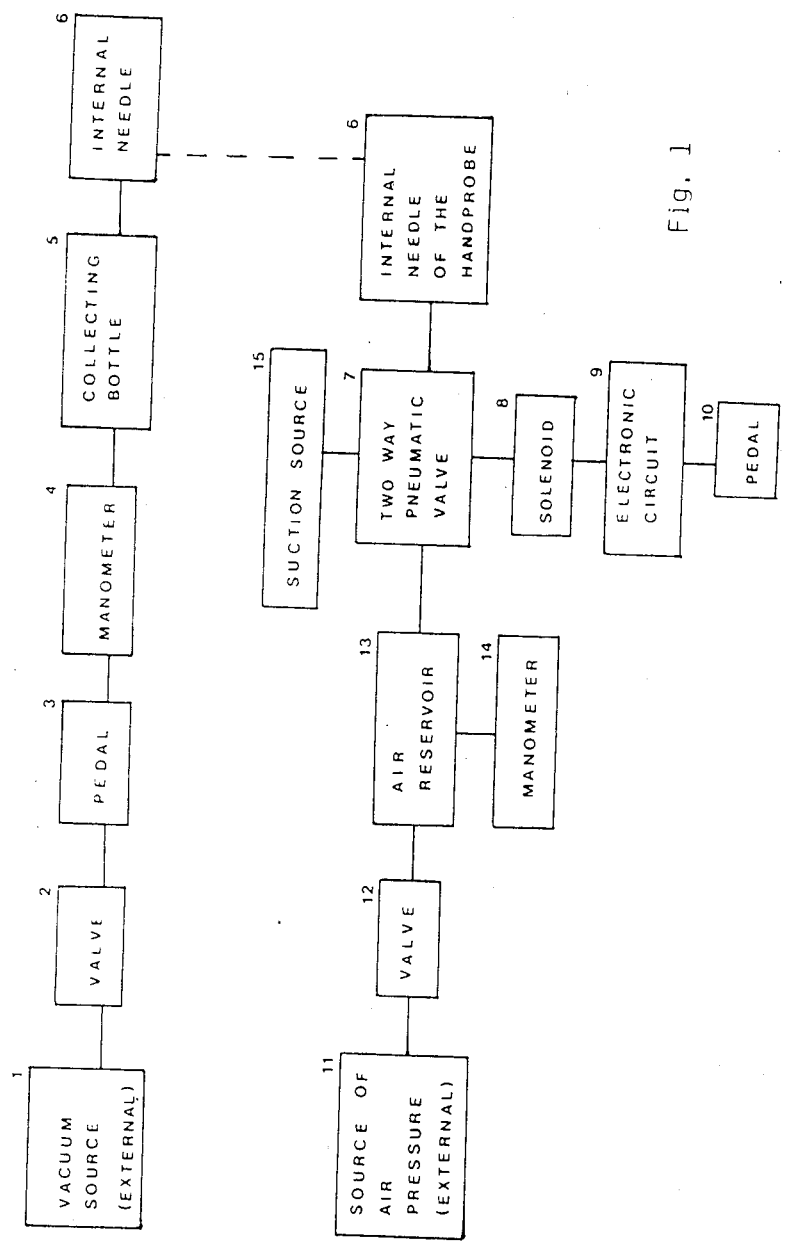
FIG. 1 is a schematic representation of the components of the pneumatic module for intraocular microsurgery.

Referring to the drawing in detail, it can be observed that it is composed of two sub-units in which reference numerals designate the components.

DETAILED DESCRIPTION OF THE PREFERRED EMBODIMENT

Unit A is responsible for aspirating the severed material. It comprises a pressure valve 2 that vents out the excess of suction admitted in the console. Valve 2 is interposed between vacuum source 1, which is independent and external to the pneumatic console, and a controller, pedal 3, which is provided with a pneumatic valve that permits a gradual control of the level of suction of the severed material. Pedal 3 is connected to manometer 4, which in turn is connected to collecting bottle 5, which receives the material being removed from the ocular globe. Internal needle 6 of the handprobe is connected to collecting bottle 5 through a silicone or other tubing.

Unit B is responsible for the reciprocating movement of the internal needle. It includes a two-way pneumatic valve 7 controlled by solenoid 8, which alternates the vacuum and air pressure flows that make the internal needle of the probe reciprocate. The electronic circuit 9 commands the solenoid 8 and controls in this way the frequency of alternation of the vacuum and air pressure flows. That is, electronic circuit 9 controls the cutting frequency of the probe. A controller in the form of pedal 10 turns on and off circuit 9. A source of air pressure 11, which is not contained within the module, supplies pressure valve 12 with an air flow. Pressure valve 12 controls the level of air pressure that is admitted into the handprobe, thus permitting the use of different probes, according to their different working pressures. Air reservoir 13, which is connected to valve 12, makes more uniform the air flow that is admitted into the pneumatic valve 7. Manometer 14 reads the level of air pressure that is admitted into the pneumatic valve 7. The level of air pressure is the same as the level present inside the air reservoir 13. The other flow that is admitted into the pneumatic valve 7 comes from a suction source, such as vacuum pump 15. The vacuum flow is intercalated with the air pressure flow by means of the two-way pneumatic valve 7 and the solenoid 8. The resultant alternating flow is driven to the piston of the handprobe and makes the internal needle 6 of the probe reciprocate.

Valve 12 allows one to vary the pressure operating the probe. Various probes have different operating pressures (e.g. from 0 to 30 p.s.i. or more). It is necessary to be able to vary the operating pressure to accommodate the different available probes. This may be important for at least three reasons. First, one may want to use different probes for different aspects of the same surgery. Second, if a probe breaks, one can use a different make probe with a different operating pressure from the single console of this invention. Third, a single console would be useful for training new surgeons to use different probes.

The source of air pressure 11 and the vacuum source 1 are purposely not contained within the module of this invention. The air pressure and vacuum lines normally available in operating rooms can be used advantageously, permitting the unit of the present invention to be a very light and portable one. A three-pedal system permits the activation of both features, progressive aspiration and internal needle movement in a simultaneous or separate way.

Various modifications and changes may be made in the configuration described above that come within the spirit of this invention. The invention embraces all such changes and modifications coming within the scope of the appended claims.

I claim:

1. A pneumatic module for controlling an intraocular microsurgery probe, which severs and removes material from an eye, the module comprising:
   (a) a first unit for aspirating suctioned material from an eye comprising:
      (i) pressure valve means for venting out any excess suction in the eye, the pressure valve controlling an upstream vacuum source;
      (ii) mechanically controlled pneumatic valve means downstream from the pressure valve means for permitting the control of the level of suction of the material being severed by the probe; and
      (iii) vacuum display means connected to the pneumatic valve means for displaying the level of suction at the probe, the module further comprising
   (b) a second unit for reciprocating an internal needle in the probe, the second unit comprising:

(i) pneumatic valve means downstream from a source of air pressure for permitting control of the level of air pressure that is channeled to the probe;

(ii) an air reservoir downstream from the pneumatic valve means;

(iii) a manometer operably connected to the air reservoir for gauging the pressure level of the air pressure flow; and (iv) a two-way valve alternately receiving pressurized air from an air reservoir and receiving a vacuum flow from a second source of vacuum;

(v) an electronic circuit operably connected to the two-way valve for controlling the frequency that the two-way valve alternates between the vacuum flow and air pressure flow.

* * * * *